United States Patent
Mitsuhashi et al.

(10) Patent No.: US 11,977,043 B2
(45) Date of Patent: May 7, 2024

(54) MEMS TYPE SEMICONDUCTOR GAS DETECTION ELEMENT

(71) Applicant: NEW COSMOS ELECTRIC CO., LTD., Osaka (JP)

(72) Inventors: Hirokazu Mitsuhashi, Osaka (JP); Naganori Dogami, Osaka (JP)

(73) Assignee: NEW COSMOS ELECTRIC CO., LTD. (JP)

( * ) Notice: Subject to any disclaimer, the term of this patent is extended or adjusted under 35 U.S.C. 154(b) by 687 days.

(21) Appl. No.: 17/253,024

(22) PCT Filed: Aug. 2, 2019

(86) PCT No.: PCT/JP2019/030567
§ 371 (c)(1),
(2) Date: Dec. 16, 2020

(87) PCT Pub. No.: WO2020/031909
PCT Pub. Date: Feb. 13, 2020

(65) Prior Publication Data
US 2021/0116405 A1    Apr. 22, 2021

(30) Foreign Application Priority Data

Aug. 7, 2018  (JP) .................................. 2018-148446

(51) Int. Cl.
*G01N 27/12* (2006.01)
*B81B 3/00* (2006.01)
(Continued)

(52) U.S. Cl.
CPC ......... *G01N 27/129* (2013.01); *B81B 3/0035* (2013.01); *G01N 27/12* (2013.01);
(Continued)

(58) Field of Classification Search
CPC .... G01N 27/129; G01N 27/12; G01N 27/414; G01N 33/005; G01N 33/004;
(Continued)

(56) References Cited

U.S. PATENT DOCUMENTS

| | | | |
|---|---|---|---|
| 4,608,549 A | 8/1986 | Fukui | |
| 6,596,236 B2 * | 7/2003 | DiMeo, Jr. ............. | G01N 21/59 |
| | | | 73/31.06 |

(Continued)

FOREIGN PATENT DOCUMENTS

| | | | | |
|---|---|---|---|---|
| CN | 102037349 A | | 4/2011 | |
| CN | 109906373 A | * | 6/2019 | ........... G01N 27/125 |

(Continued)

OTHER PUBLICATIONS

International Search Report in English, Application No. PCT/JP2019/030567, dated Oct. 29, 2019, 2 pages.

(Continued)

*Primary Examiner* — Stephanie E Bloss
*Assistant Examiner* — Kevin C Butler
(74) *Attorney, Agent, or Firm* — Ware, Fressola, Maguire & Barber LLP

(57) ABSTRACT

The MEMS type semiconductor gas detection element of the invention is a MEMS type semiconductor gas detection element 1 having a MEMS structure, for detecting hydrogen gas, comprising: a substrate 2; a gas sensitive portion 3 mainly made of a metal oxide semiconductor and provided to the substrate 2; a heating portion 4 for heating the gas sensitive portion 3; an inactive film 5 having hydrogen-permselective and formed outside the gas sensitive portion 3; a protective film 6 formed outside the inactive film 5, for suppressing deterioration of the gas sensitive portion 3.

5 Claims, 10 Drawing Sheets

(51) Int. Cl.
*G01N 27/414* (2006.01)
*G01N 33/00* (2006.01)

(52) U.S. Cl.
CPC ......... *G01N 27/122* (2013.01); *G01N 27/414* (2013.01); *G01N 33/004* (2013.01); *G01N 33/005* (2013.01); *B81B 2201/02* (2013.01); *B81B 2201/10* (2013.01)

(58) Field of Classification Search
CPC ...... G01N 33/122; B81B 3/0035; B81B 3/02; B81B 3/10
USPC ........................................................ 73/31.06
See application file for complete search history.

(56) References Cited

U.S. PATENT DOCUMENTS

| | | | | |
|---|---|---|---|---|
| 7,370,511 | B1 * | 5/2008 | Chen | .................... G01N 27/128 |
| | | | | 73/31.05 |
| 11,567,020 | B2 * | 1/2023 | Potyrailo | ............ G01N 27/125 |
| 2006/0124448 | A1 * | 6/2006 | Jayaraman | ............ C23C 14/165 |
| | | | | 204/192.15 |
| 2009/0301879 | A1 | 12/2009 | Soundarrajan et al. | |
| 2021/0116405 | A1 * | 4/2021 | Mitsuhashi | ........... B81B 3/0035 |

FOREIGN PATENT DOCUMENTS

| | | | | | |
|---|---|---|---|---|---|
| EP | | 115183 | A * | 8/1984 | ............. G01N 27/12 |
| EP | | 0115183 | A2 * | 8/1984 | ............. G01N 27/12 |
| JP | | 59-120945 | A | 7/1984 | |
| JP | | H04-29049 | A | 1/1992 | |
| JP | | H09269306 | A * | 10/1997 | ............. G01N 27/12 |
| JP | | 11-287781 | A | 10/1999 | |
| JP | | 2003-344342 | A | 12/2003 | |
| JP | | 2004066011 | A | 3/2004 | |
| JP | | 3901594 | B2 * | 4/2007 | |
| JP | | 3929355 | B2 * | 6/2007 | |
| JP | | 2007-333625 | A | 12/2007 | |
| JP | | 2008-261634 | A | 10/2008 | |
| JP | | 2008261634 | A * | 10/2008 | |
| JP | | 4340639 | B2 * | 10/2009 | |
| JP | | 4355300 | B2 * | 10/2009 | |
| JP | | 4532671 | B2 * | 8/2010 | |
| JP | | 4910493 | B2 * | 4/2012 | |
| JP | | 5312174 | B2 * | 10/2013 | |
| JP | | 2014-41164 | A | 3/2014 | |
| JP | | 2014041164 | A * | 3/2014 | |
| JP | | 2016017741 | A | 2/2016 | |
| JP | | 2017-166902 | A | 9/2017 | |
| JP | | 2017166902 | A * | 9/2017 | |
| JP | | 6387240 | B2 * | 9/2018 | |
| KR | | 101269510 | B1 | 5/2013 | |
| WO | | 2009/126568 | A1 | 10/2009 | |
| WO | | 2018/053655 | A1 | 3/2018 | |
| WO | | WO-2018053655 | A1 * | 3/2018 | ........... G01N 27/125 |

OTHER PUBLICATIONS

Extended European Search Report, application No. 19847126.0, dated Nov. 23, 2021, 8 pages.

Notification of Transmittal of Translation of the International Preliminary Report on Patentability (IPRP) including the Written Opinion of the International Searching Authority, International Application PCT/JP2019/030567, dated Feb. 18, 2021, 6 pages.

Chinese Office Action (with search report table on pp. 10-11 citing nine patent documents with relevance categories "Y" & "A" indicated), Application No. 201980030786.2, dated Dec. 28, 2023, 12 pages.

Machine translation of Chinese Office Action (without search report table), Application No. 201980030786.2, 9 pages.

* cited by examiner (Example 1)

(Example 2)

(Example 3)

(Example 4)

(Comparative Example 2)

(Comparative Example 1)

(Example 4)

MEMS TYPE SEMICONDUCTOR GAS DETECTION ELEMENT

TECHNICAL FIELD

The invention relates to a MEMS type semiconductor gas detection element.

BACKGROUND ART

Conventionally, gas detection elements for detecting gas, such as a coil type semiconductor gas detection element disclosed in Patent Document 1 and a MEMS (Micro Electro Mechanical System) type semiconductor gas detection element disclosed in Patent Document 2 have been used. They are common in that the both semiconductor gas detection elements detect a detection object gas by detecting an electric resistance change caused by an interaction between a gas sensitive portion comprising a metal oxide semiconductor and the detection object gas. On the other hand, they are different in that a coil type semiconductor gas detection element has an advantage that it has a simple structure and easy to produce, while a MEMS type semiconductor gas detection element has an advantage that it is small in size and consumes less power.

For the coil type and MEMS type semiconductor gas detection elements, a technique for detecting hydrogen gas with priority while reducing effects of other gases is required in order to detect hydrogen gas accurately in a gas detection environmental atmosphere containing hydrogen gas, methane gas, ethanol, and others. For this purpose, for example, in the coil type semiconductor gas detection element, as shown in Patent Document 1, an inactive film comprising silica is provided outside the gas sensitive portion. This inactive film allows permeation of hydrogen gas, which is smaller in molecular size, with priority and suppresses permeation of methane gas, ethanol, and others, which are larger in molecular size. Therefore, the coil type semiconductor gas detection element can obtain high sensitivity and selectivity to hydrogen gas by providing such inactive film outside the gas sensitive portion.

PRIOR ART DOCUMENT

Patent Document

Patent Document 1: JP 2003-344342 A
Patent Document 2: JP 2014-041164 A

SUMMARY OF THE INVENTION

However, in the MEMS type semiconductor gas detection element, if the inactive film is provided outside the gas sensitive portion same as in the coil type semiconductor gas detection element, the sensitivity to hydrogen gas is improved, but a problem arises that a response recovery characteristic to hydrogen gas is declined. On the other hand, if the inactive film is formed to be thin to suppress the decline of the response recovery characteristic to hydrogen gas, a problem arises that the sensitivity to hydrogen gas is declined and deterioration of the gas sensitive portion becomes more likely to occur. This is a problem typical of the MEMS type semiconductor gas detection element, and it is considered that this may be caused by the element size and operation condition of the MEMS type semiconductor gas detection element.

The invention is made in consideration of the above problem and aims to provide a MEMS type semiconductor gas detection element that suppresses deterioration of the gas sensitive portion while maintaining the hydrogen selectivity.

The MEMS type semiconductor gas detection element of the invention is a MEMS type semiconductor gas detection element having a MEMS structure, for detecting hydrogen gas, comprising: a substrate; a gas sensitive portion mainly made of a metal oxide semiconductor and provided to the substrate; a heating portion for heating the gas sensitive portion; an inactive film having hydrogen-permselective and formed outside the gas sensitive portion; a protective film formed outside the inactive film, for suppressing deterioration of the gas sensitive portion.

EMBODIMENT FOR CARRYING OUT THE INVENTION

In the following, a MEMS type semiconductor gas detection element according to an embodiment of the invention is explained in reference to the accompanying drawings. However, the embodiment shown in the following is exemplary, and the MEMS type semiconductor gas detection element of the invention is not limited to the following examples.

The MEMS type semiconductor gas detection element of the embodiment is used for detecting hydrogen gas contained in an environmental atmosphere such as an atmospheric air. The MEMS type semiconductor gas detection element utilizes a resistance value (or electric conductivity) that changes in accordance with a chemical reaction between oxygen adsorbed on a surface thereof and hydrogen gas in the environmental atmosphere to detect the hydrogen gas.

Figure 1:
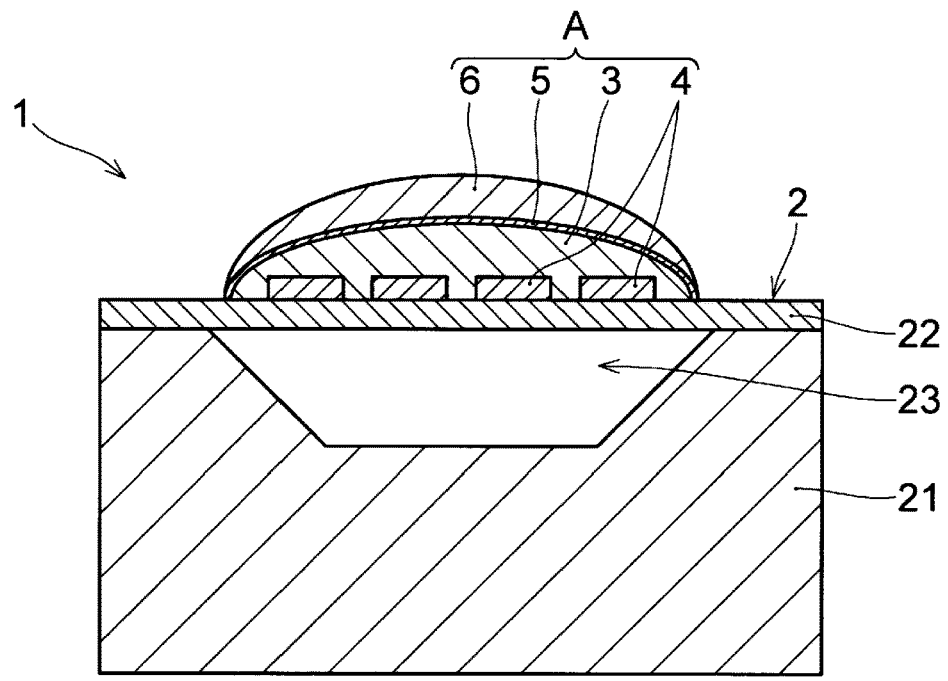
FIG. 1 is a schematic cross-sectional view of a MEMS type semiconductor gas detection element according to an embodiment of the invention.

As shown in FIG. 1, the MEMS type semiconductor gas detection element 1 has a MEMS (Micro Electro Mechanical System) structure. The MEMS structure means a device structure in which at least some of components of the element are integrated on a substrate such as silicon substrate by a micromachining technique. Compared to a coil type semiconductor gas detection element, the MEMS type semiconductor gas detection element 1 can be smaller in size and be driven with lower power consumption by having the MEMS structure.

As shown in FIG. 1, the MEMS type semiconductor gas detection element 1 comprises a substrate 2, a gas sensitive portion 3 provided to the substrate 2, a heating portion 4 for heating the gas sensitive portion 3, an inactive film 5 formed outside the gas sensitive portion 3, and a protective film 6 formed outside the inactive film 5.

The MEMS type semiconductor gas detection element 1 is incorporated, for example, in a known bridge circuit and detect a change in the resistance value in accordance with the chemical reaction between the adsorbed oxygen on the surface of the gas sensitive portion 3 and the hydrogen gas in the environmental atmosphere. The MEMS type semiconductor gas detection element 1 uses the heating portion 4 as an electrode or is provided with an electrode separate from the heating portion 4 for detecting the change in the resistance value of the gas sensitive portion 3, and is incorporated in the bridge circuit. The bridge circuit measures a change in the potential difference in the circuit resulting from the change in the resistance value in the MEMS type semiconductor gas detection element 1 with a potentiometer and outputs the change in the potential difference as a hydrogen gas detection signal. However, the circuit in which the MEMS type semiconductor gas detection element 1 is to be incorporated is not limited to the bridge circuit as long as it can detect the change in the resistance value in accordance with the chemical reaction between the adsorbed oxygen on the surface of the gas sensitive portion 3 and the hydrogen gas. The MEMS type semiconductor gas detection element 1 may be incorporated in a circuit different from the bridge circuit to be used.

The substrate 2 is a member for holding the gas sensitive portion 3, the heating portion 4, the inactive film 5, and the protective film 6 (hereinafter, which are also collectively referred to as a "laminated body A") in such a way that they are electrically insulated to the substrate 2. As shown in FIG. 1, in the embodiment, the substrate 2 comprises a substrate main body 21, an insulating support layer 22 provided on the substrate main body 21, and a cavity portion 23 provided beneath a part of the insulating support layer 22. The substrate main body 21 supports the insulating support layer 22, and the insulating support layer 22 supports the laminated body A so that the laminated body A is electrically insulated to the substrate main body 21. The laminated body A is provided above the part of the insulating support layer 22 under which the cavity portion 23 is provided. In the MEMS type semiconductor gas detection element 1, since the laminated body A is provided at the part of the insulating support layer 22 on the cavity portion 23, the conduction of the heat applied to the laminated body A to the substrate main body 21 can be suppressed, and thus the laminated body A can be heated efficiently, thereby allowing for low power consumption for driving.

The insulating support layer 22 for supporting the laminated body A is not particularly limited as long as it is configured so that the laminated body A is electrically insulated to the substrate body 21. For example, insulating material may be provided only on a surface layer of the insulating support layer 22 on which the laminated body A is provided, or the insulating support layer 22 may be made of insulating material entirely. In the embodiment, the substrate main body 21 is made of silicon, and the insulating support layer 22 is made of silicon oxide. However, the substrate 2 is not limited to the embodiment as long as it holds the laminated body A in such a way that the laminated body A is electrically insulated to the substrate 2. The substrate may be made of insulating material entirely, such as a glass substrate.

The gas sensitive portion 3 is mainly made of a metal oxide semiconductor and is a portion where the electric resistance is changed in accordance with the chemical reaction between the adsorbed oxygen on the surface thereof and the hydrogen gas. As shown in FIG. 1, in the embodiment, the gas sensitive portion 3 is provided on the substrate 2 to cover the heating portion 4. The method for providing the gas sensitive portion 3 is not particularly limited as long as it is provided so that it can be heated on the substrate 2 by the heating portion 4. The gas sensitive portion 3 may be formed by, for example, applying and drying on the substrate 2 a paste made by mixing fine powder of the metal oxide semiconductor with solvent. The gas sensitive portion 3 may be also formed with a known film deposition technique such as a sputtering.

The metal oxide semiconductor of the gas sensitive portion 3 is not particularly limited as long as its electric resistance changes in accordance with the chemical reaction between the adsorbed oxygen and the hydrogen gas. For example, from the viewpoint of facilitating the oxygen adsorption and the chemical reaction between the adsorbed oxygen and a gas component and of improving a gas detection sensitivity, as the metal oxide semiconductor of the gas sensitive portion 3, preferably N-type semiconductor is used, more preferably a metal oxide semiconductor comprising at least one selected from tin oxide, indium oxide, zinc oxide and tungsten oxide is used, and further preferably a metal oxide semiconductor comprising at least one selected from tin oxide and indium oxide is used. The metal oxide semiconductor of the gas sensitive portion 3 may comprise one or more of the above-mentioned metal oxide semiconductors.

The metal oxide semiconductor of the gas sensitive portion 3 may be added with a metallic element as a donor for adjusting the electric resistance thereof. The metallic element to be added is not particularly limited as long as it can be added in the metal oxide semiconductor as the donor for adjusting the electric resistance of the metal oxide semiconductor. As the metallic element, at least one selected from, for example, antimony, niobium and tungsten is exemplified. Further, oxygen deficiency may be introduced in the metal oxide semiconductor of the gas sensitive portion 3 for adjusting the electric resistance. The metallic element concentration and the oxygen deficiency concentration can be suitably set in accordance with a required electric resistance.

The metal oxide semiconductor of the gas sensitive portion 3 may be added with a metal oxide having high oxidation activity as a material to be carried by the metal oxide semiconductor. By adding the metal oxide having high oxidation activity to the metal oxide semiconductor of the gas sensitive portion 3, the surface activity of the metal oxide semiconductor can be increased. It is considered that this may be because by adding the metal oxide having high oxidation activity to the metal oxide semiconductor, the metal oxide semiconductor becomes less hydrophilic and the metal oxide semiconductor becomes moderately hydrophobic, and thus an absorption activity of water to the metal oxide semiconductor is suppressed and an oxidation activity of the metal oxide semiconductor is stabilized. As the metal oxide to be added, at least one selected from chromium oxide, cobalt oxide, iron oxide, rhodium oxide, copper oxide, palladium oxide, cerium oxide, platinum oxide, tungsten oxide and lanthanum oxide is exemplified. Among those, at least one selected from chromium oxide, cobalt oxide and iron oxide is preferable.

The heating portion 4 is a portion for heating the gas sensitive portion 3. As shown in FIG. 1, in the embodiment, the heating portion 4 is provided on the insulating support layer 22 of the substrate 2 and covered by the gas sensitive portion 3. The heating portion 4 is made of a noble metal such as platinum, platinum-rhodium alloy and is configured to generate heat when energized to heat the gas sensitive portion 3. In the embodiment, the heating portion 4 also functions as an electrode for detecting the resistance value change of the gas sensitive portion 3. However, the heating portion 4 is not particularly limited in its arrangement and constituent material to the above example as long as it is configured to heat the gas sensitive portion 3. For example, the heating portion 4 may be provided on an undersurface of the insulating support layer 22 of the substrate 2 separately from an electrode for detecting the resistance value change of the gas sensitive portion 3.

The inactive film 5 is a hydrogen-permselective film. The inactive film 5 allows permeation of the hydrogen gas, which has a relatively small molecular size, and suppresses permeation of other interference gases having relatively large molecular size (e.g., carbon monoxide, ethanol, methane, butane). The inactive film 5 suppresses a chemical reaction between the adsorbed oxygen on the surface of the gas sensitive portion 3 and gases other than the hydrogen gas by suppressing permeation of the gases other than hydrogen gas. The MEMS type semiconductor gas detection element 1 improves the selectivity to the hydrogen gas by providing the inactive film 5 outside the gas sensitive portion 3.

The inactive film 5 is not particularly limited as long as it is formed outside the gas sensitive part 3. The inactive film 5 is preferably formed with a thickness that allows suppression of a decline of a response characteristic and/or response recovery characteristic of the gas sensitive portion 3 to the hydrogen gas while maintaining a hydrogen selectivity required for the MEMS type semiconductor gas detection element 1. It is to be noted that the response characteristic to the hydrogen gas means how quickly a sensor output corresponding to the hydrogen gas is obtained when the hydrogen gas is introduced into the measurement environmental atmosphere. In other words, it can be said that the shorter the time (a response time) to obtain a sensor output corresponding to the concentration of the introduced hydrogen gas after the introduction of the hydrogen gas is, the better the response characteristic is. In addition, the response recovery characteristic to the hydrogen gas means that, when the measurement environmental atmosphere is replaced with a measurement environmental atmosphere without hydrogen gas after the detection of the hydrogen gas, how quickly the sensor output returns to a sensor output corresponding to the measurement environmental atmosphere without hydrogen gas since the replacement of the measurement environmental atmosphere. In other words, it can be said that the shorter the time (a response recovery time) to return to the sensor output corresponding to the measurement environmental atmosphere without hydrogen gas after the replacement of the measurement environmental atmosphere is, the better the response recovery characteristic is.

Figure 2:
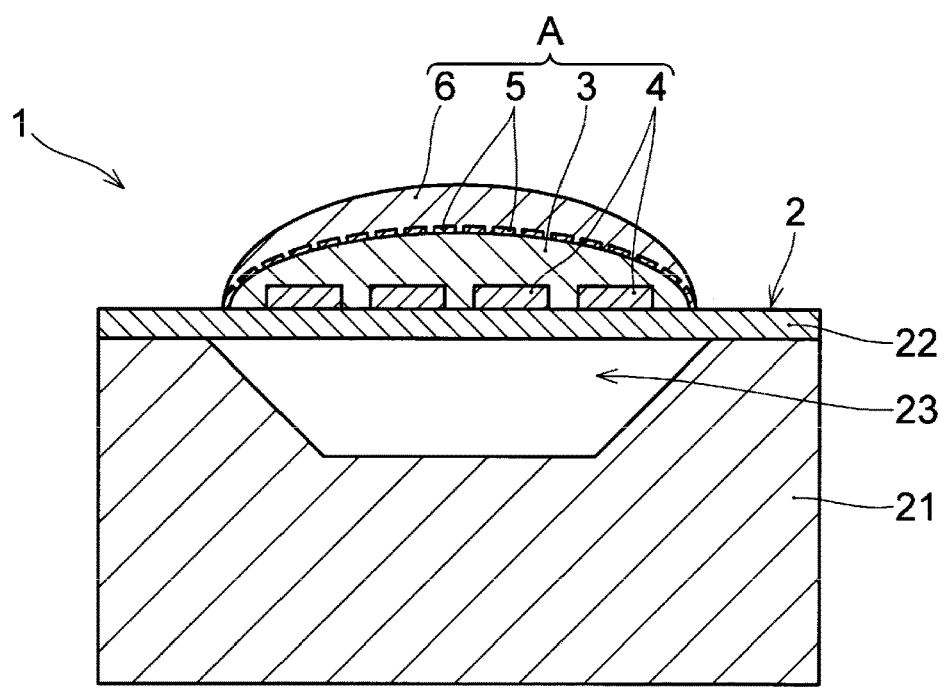
FIG. 2 is a schematic cross-sectional view of a MEMS type semiconductor gas detection element according to another embodiment of the invention.

From the viewpoint mentioned above, the inactive film 5 is, for example, as shown in FIG. 2, preferably formed at a part of the gas sensitive portion 3. For example, the inactive film 5 preferably is an island-shaped film on the gas sensitive portion 3, which is formed in an early stage of a film formation such as gas-phase processing, or a porous film having many (or innumerable) pinholes on the gas sensitive portion 3, which is formed in an stage before further growing into a uniform film. By providing the inactive film 5 at a part of the gas sensitive portion 3, it is possible to suppress the decline of the response characteristic and/or response recovery characteristic of the gas sensitive portion 3 to the hydrogen gas while maintaining the hydrogen selectivity of the MEMS type semiconductor gas detection element 1 within a predetermined range. The cause of this can be considered as follows. As mentioned above, since the inactive film suppresses permeation of the gases other than hydrogen gas, the inactive film might limit an escape of water molecules out of the gas sensitive portion, which may be generated by the chemical reaction that causes the resistance value change of the gas sensitive portion. If the water molecules remain on the surface of the gas sensitive portion or in the inactive film, the adsorption of oxygen molecules, which is required for a reaction causing the resistance value change of the gas sensitive portion, is also limited. In the case of a coil type semiconductor gas detection element, since sufficient heating process can be performed even with a thick inactive film being provided, it is possible to facilitate desorption of the water molecules. However, in the case of a MEMS type semiconductor gas detection element, it is considered that it is difficult to perform sufficient desorption of the water molecules since it is not possible to perform sufficient heat processing for achieving low power consumption for driving. If the water molecules remain on the surface of the gas sensitive portion or in the inactive film, the response characteristic and/or response recovery characteristic to the hydrogen gas may decline. In the MEMS type semiconductor gas detection element 1 of the embodiment, it is considered that since the inactive film 5 is formed at a part of the gas sensitive portion 3, the passage of the water molecules and oxygen molecules can be facilitated at least at a location where the inactive film 5 is not provided, and the limitation of the passage of the water molecules and oxygen molecules can be suppressed as a whole, allowing suppression of the decline of the response characteristic and/or response recovery characteristic to the hydrogen gas.

From the viewpoint of suppressing the decline of the response characteristic and/or response recovery characteristic to the hydrogen gas, the inactive film 5 is preferably formed on an outer surface part of the gas sensitive portion 3. The outer surface part of the gas sensitive portion 3 may be structured as a part at the outside of the gas sensitive portion 3, which comprises a metal constituting the metal oxide semiconductor of the gas sensitive portion 3 and an element constituting the inactive film 5. For example, the inactive film 5 may be structured as a part formed by a chemical reaction between an outer surface side of the gas sensitive portion 3 and the inactive film 5. By forming the inactive film 5 only at the outer surface part of the gas sensitive portion 3, it is possible to further suppress the decline of the response characteristic and/or response recovery characteristic to the hydrogen gas. It is considered that this may be because by forming the inactive film 5 only at the outer surface part of the gas sensitive portion 3, the limitation of the passage of the water molecules and oxygen molecules can be suppressed.

The inactive film 5 is not particularly limited as long as it has hydrogen selectivity. The inactive film 5 preferably comprises a silica film having a siloxane bond. The silica film can be formed, for example, when the gas sensitive portion 3 is heated in an atmosphere containing 1 to 500 ppm of hexamethyldisiloxane (hereinafter, referred to as "HMDS"), which is one of siloxane compounds of silicon. The heating of the gas sensitive portion 3 is adjusted to the decomposition temperature of the HMDS or higher by energizing the heating portion 4 to generate the Joule Heat. More specifically, by heating the gas sensitive portion 3 to a temperature of about 500 to 550° C. and thermally decomposing the HMDS outside the gas sensitive portion 3 for a predetermined duration of time, the silica film having the siloxane bond can be formed outside the gas sensitive portion 3. The concentration of HMDS in the environmental atmosphere, the temperature of the gas sensitive portion 3, and the reaction time are suitably adjusted for forming the silica film having a thickness that can suppress the decline of the response characteristic and/or response recovery characteristic of the gas sensitive portion 3 to the hydrogen gas while maintaining the required hydrogen selectivity, or for forming the silica film at a part or an outer surface part of the gas sensitive portion 3. For forming the silica film having the siloxane bond, for example, silicon compounds, such as halosilane, alkylsilane, alkylhalosilane, or silylalkoxide, other than HMDS may be used.

The protective film 6 suppresses deterioration of the gas sensitive portion 3. For example, the protective film 6 suppresses a change over time in the detection sensitivity of the gas sensitive portion 3 to the hydrogen gas or suppresses deterioration over time of the response characteristic and/or response recovery characteristic of the gas sensitive portion 3 to the hydrogen gas. Here, as mentioned above, when the MEMS type semiconductor gas detection element is provided with the inactive film outside the gas sensitive portion, the sensitivity to the hydrogen gas is improved, whereas the problem of declining of the response characteristic and/or response recovery characteristic to the hydrogen gas arises. On the other hand, when the inactive film is formed to be thin to suppress the decline of the response characteristic and/or response recovery characteristic to the hydrogen gas while maintaining the sensitivity to the hydrogen gas within a predetermined range, a problem arises that deterioration of the gas sensitive portion becomes more likely to occur. It is considered that this may be because interference gases other than the hydrogen gas enter the inactive film 5 over time and are captured in the inactive film 5, thereby further preventing the above-mentioned passage of the water molecules and oxygen molecules. Therefore, by forming the protective film 6 outside the inactive film 5, the protective film 6 may suppress interference gases other than the hydrogen gas from reaching to the inactive film 5 over time, thereby maintaining an initial state of the inactive film 5 and suppressing deterioration of the gas sensitive portion 3.

The constituting material of the protective film 6 is not particularly limited as long as the protective film 6 can suppress deterioration of the gas sensitive portion 3. The protective film 6, for example, may be made of an insulating metal oxide. By making the protective film 3 with the insulating metal oxide, an electric current flow into the protective film 6 can be suppressed, and the influence on the resistance value change of the gas sensitive portion 3 at the time of the hydrogen gas detection can be reduced, whereby the deterioration of the gas sensitive portion 3 can be suppressed while reducing influence of the gas sensitive portion 3 on the hydrogen gas detection. As the insulating metal oxide, alumina, silica, and a complex oxide containing aluminum and silicon are exemplified without limitation. Among those, the complex oxide containing aluminum and silicon, which has a large specific surface area, is preferable. As the complex oxide containing aluminum and silicon, aluminosilicate and others are exemplified. By adopting the complex oxide containing aluminum and silicon, which has a large specific surface area, as a material of the protective film 6, the deterioration of the gas sensitive portion 3 can be further suppressed. It is considered that this may be because the interference gases other than the hydrogen gas are easily captured in the complex oxide containing aluminum and silicon, and accordingly the initial state of the inactive film 5 can be maintained more easily.

The protective film 6 may be formed with an insulating metal oxide carrying a metal oxide having oxidation activity. The protective film 6, by being formed with the insulating metal oxide carrying the metal oxide having oxidation activity, can further suppress the deterioration of the gas sensitive portion 3. It is considered that this may be because the oxidation activity of the metal oxide decomposes a specific gas component other than the hydrogen gas, thereby suppressing the entry of the specific gas component into the inactive film 5. As the insulating metal oxide carrying the metal oxide, silica, alumina, and a complex oxide containing aluminum and silicon are exemplified, as mentioned above. Among those, the complex oxide containing aluminum and silicon, which has a large specific surface area and an excellent capacity of carrying the metal oxide, is preferable. As the complex oxide containing aluminum and silicon, aluminosilicate and others are exemplified. As the metal oxide having oxidation activity, at least one selected from chromium oxide, palladium oxide, cobalt oxide, iron oxide, rhodium oxide, copper oxide, cerium oxide, platinum oxide, tungsten oxide and lanthanum oxide is exemplified. Among those shown above, in the viewpoint of improving the response characteristic and/or response recovery characteristic of the gas sensitive portion 3 and suppressing the deterioration over time of the response characteristic and/or response recovery characteristic of the gas sensitive portion 3, chromium oxide or palladium oxide is preferable as the metal oxide.

In the embodiment, as shown in FIG. 1 and FIG. 2, the protective film 6 is provided on the substrate 2 to cover the gas sensitive portion 3 and the inactive film 5. However, the protective film 6 may be sufficient if it is provided at least outside the inactive film 5 so as to suppress the deterioration of the gas sensitive portion 3. For example, the protective film 6 may be provided to cover only a part of the gas sensitive part 3 and inactive film 5. In the case where the protective film 6 is made of the insulating metal oxide, the protective film 6 may be formed by applying and drying on the gas sensitive portion 3 and inactive film 5 a paste made by mixing fine powder of the insulating metal oxide with solvent. In the case where the protective film 6 is made of the insulating metal oxide and the metal oxide, the protective film 6 may be formed by applying and drying on the gas sensitive portion 3 and inactive film 5 a paste made by mixing fine powder containing the insulating metal oxide and the metal oxide with solvent. Alternatively, it is also possible to form the protective film 6 with a known film deposition technique such as a sputtering.

So far, the MEMS type semiconductor gas detection element according to an embodiment of the invention is explained. However, the MEMS type semiconductor gas detection element of the invention is not limited to the above-mentioned embodiment. The above-mentioned embodiment mainly describes an invention having the following configurations.

(1) A MEMS type semiconductor gas detection element having a MEMS structure, for detecting hydrogen gas, comprising a substrate; a gas sensitive portion mainly made of a metal oxide semiconductor and provided to the substrate; a heating portion for heating the gas sensitive portion; an inactive film having hydrogen-permselective and formed outside the gas sensitive portion; and a protective film formed outside the inactive film, for suppressing deterioration of the gas sensitive portion.

According to the configuration of (1), the MEMS type semiconductor gas detection element can suppress deterioration of the gas sensitive portion while maintaining the hydrogen selectivity.

(2) The MEMS type semiconductor gas detection element of (1), characterized in that the protective film is configured to suppress deterioration over time of a response characteristic and/or response recovery characteristic of the gas sensitive portion to hydrogen gas.

According to the configuration of (2), the MEMS type semiconductor gas detection element can further suppress deterioration over time of the response characteristic and/or response recovery characteristic of the gas sensitive portion to hydrogen gas.

(3) The MEMS type semiconductor gas detection element of (1), characterized in that the protective film comprises alumina or a complex oxide containing aluminum and silicon.

According to the configuration of (3), the MEMS type semiconductor gas detection element can further suppress deterioration of the gas sensitive portion while reducing influence of the gas sensitive portion on the hydrogen gas detection.

(4) The MEMS type semiconductor gas detection element of any of (1) to (3), characterized in that the inactive film is formed at a part of the gas sensitive portion.

According to the configuration of (4), the MEMS type semiconductor gas detection element can further suppress a decline of the response characteristic and/or response recovery characteristic of the gas sensitive part to hydrogen gas.

(5) The MEMS type semiconductor gas detection element of any of (1) to (4), characterized in that the inactive film is formed at an outer surface part of the gas sensitive portion.

According to the configuration of (5), the MEMS type semiconductor gas detection element can further suppress a decline of the response characteristic and/or response recovery characteristic of the gas sensitive portion to hydrogen gas.

(6) The MEMS type semiconductor gas detection element of any of (1) to (5), characterized in that the protective film is made of a carrier made of a complex oxide containing aluminum and silicon carrying chromium oxide or palladium oxide.

According to the configuration of (6), the MEMS type semiconductor gas detection element can further improve the response characteristic and/or response recovery characteristic of the gas sensitive portion and suppress deterioration over time of the response characteristic and/or response recovery characteristic of the gas sensitive portion.

(7) The MEMS type semiconductor gas detection element of any of (1) to (6), characterized in that the inactive film comprises a silica film having a siloxane bond.

According to the configuration of (7), the MEMS type semiconductor gas detection element can further suppress deterioration of the gas sensitive portion while maintaining the hydrogen selectivity.

EXAMPLE

In the following, the excellent effect of the MEMS type semiconductor gas detection element of the embodiment is described based on examples. It should be noted, however, the MEMS type semiconductor gas detection element of the invention is not limited to the following examples.

Example 1

The MEMS type semiconductor gas detection element 1 shown in FIG. 1 was prepared. The constitutions of the MEMS type semiconductor gas detection element 1 other than the gas sensitive portion 3 and protective film 6 were prepared with a silicon substrate as the substrate 2 and a platinum wire as the heating portion 4 using a known MEMS technique.

The gas sensitive portion 3 was made by applying a paste containing fine powder of tin oxide semiconductor with 0.2 wt % of antimony added as a donor so that it covers the heating portion 4 on the substrate 2 with the maximum thickness of 40 µm and, after drying it, heating it with an electric furnace at 650° C. for two hours to sinter the tin oxide semiconductor.

As the inactive film 5, a silica film having a siloxane bond was formed outside the gas sensitive portion 3, by heating the gas sensitive portion 3 at 500° C. for one hour with Joule heat generated by energizing the heating portion 4 in an atmosphere containing 10 to 500 ppm of HMDS.

The protective film 6 was made by applying a paste containing fine powder of commercially available alumina so that it covers the inactive film 5 on the substrate 2 with the maximum thickness of 40 µm and, after drying it, heating it at 650° C. for two hours with Joule heat generated by energizing the heating portion 4 to sinter the alumina.

Example 2

The MEMS type semiconductor gas detection element 1 shown in FIG. 1 was prepared in the same manner as Example 1 except the protective film 6. The protective film 6 was made by applying a paste containing fine powder of commercially available aluminosilicate so that it covers the inactive film 5 on the substrate 2 with the maximum thickness of 40 µm and, after drying it, heating it at 650° C. for two hours with Joule heat generated by energizing the heating portion 4 to sinter the aluminosilicate.

Example 3

The MEMS type semiconductor gas detection element 1 shown in FIG. 1 was prepared in the same manner as Example 1 except the protective film 6. The protective film 6 was made by applying a paste containing fine powder made by freezing and impregnating 20 wt % of chromium oxide in commercially available aluminosilicate so that it covers the inactive film 5 on the substrate 2 with the maximum thickness of 40 μm and, after drying it, heating it at 650° C. for two hours with Joule heat generated by energizing the heating portion 4 to sinter the chromium oxide impregnated aluminosilicate.

Example 4

The MEMS type semiconductor gas detection element 1 shown in FIG.

1 was prepared in the same manner as Example 3 except the gas sensitive portion 3. The gas sensitive portion 3 was made by applying a paste made by mixing fine powder of tin oxide semiconductor with 0.2 wt % of antimony added as a donor and 2.0 wt % of fine powder of chromium oxide so that it covers the heating portion 4 on the substrate 2 with the maximum thickness of 40 μm and, after drying it, heating it with an electric furnace at 650° C. for two hours to sinter the tin oxide semiconductor carrying chromium oxide.

Comparative Example 1

A MEMS type semiconductor gas detection element without the protective film 6 of FIG. 1 was prepared. Except that the protective film 6 was not provided, the MEMS type semiconductor gas detection element was prepared in the same manner as Examples 1 to 3.

Comparative Example 2

A MEMS type semiconductor gas detection element without the protective film 6 of FIG. 1 was prepared. Except that the protective film 6 was not provided, the MEMS type semiconductor gas detection element was prepared in the same manner as Example 4.

(Evaluation of Deterioration Over Time of the Response Characteristic and Response Recovery Characteristic to Hydrogen Gas)

With the MEMS type semiconductor gas detection elements of Examples 1 to 4 and Comparative Examples 1 and 2 incorporated in a known bridge circuit, changes in the sensor output when the concentration of hydrogen gas in an atmospheric air was changed were measured. The driving condition of the MEMS type semiconductor gas detection elements was a pulse drive having a pattern of 0.06 seconds of voltage applying in a cycle of 5 seconds so that the temperature during heating was 500° C. After the concentration of hydrogen gas in the atmospheric air was changed every 1 minute to 50 ppm, 100 ppm, 200 ppm, 500 ppm, 1000 ppm, 2000 ppm, 5000 ppm, the measurement environmental atmosphere was replaced with an atmospheric air without hydrogen gas. The response characteristic was evaluated based on the rate of changes in the sensor output at timings when the concentration of hydrogen gas in the atmospheric air was changed. Also, the response recovery characteristic was evaluated based on the rate of changes in the sensor output at a timing when the environmental atmosphere having the hydrogen gas concentration of 5000 ppm was replaced with the atmospheric air without hydrogen gas. Deterioration over time of the response recovery characteristic was evaluated by conducting the above measurements immediately after the MEMS type semiconductor gas detection elements were prepared, after they were left in a room temperature for one month, and after they were left in a room temperature for two months.

Figure 3:
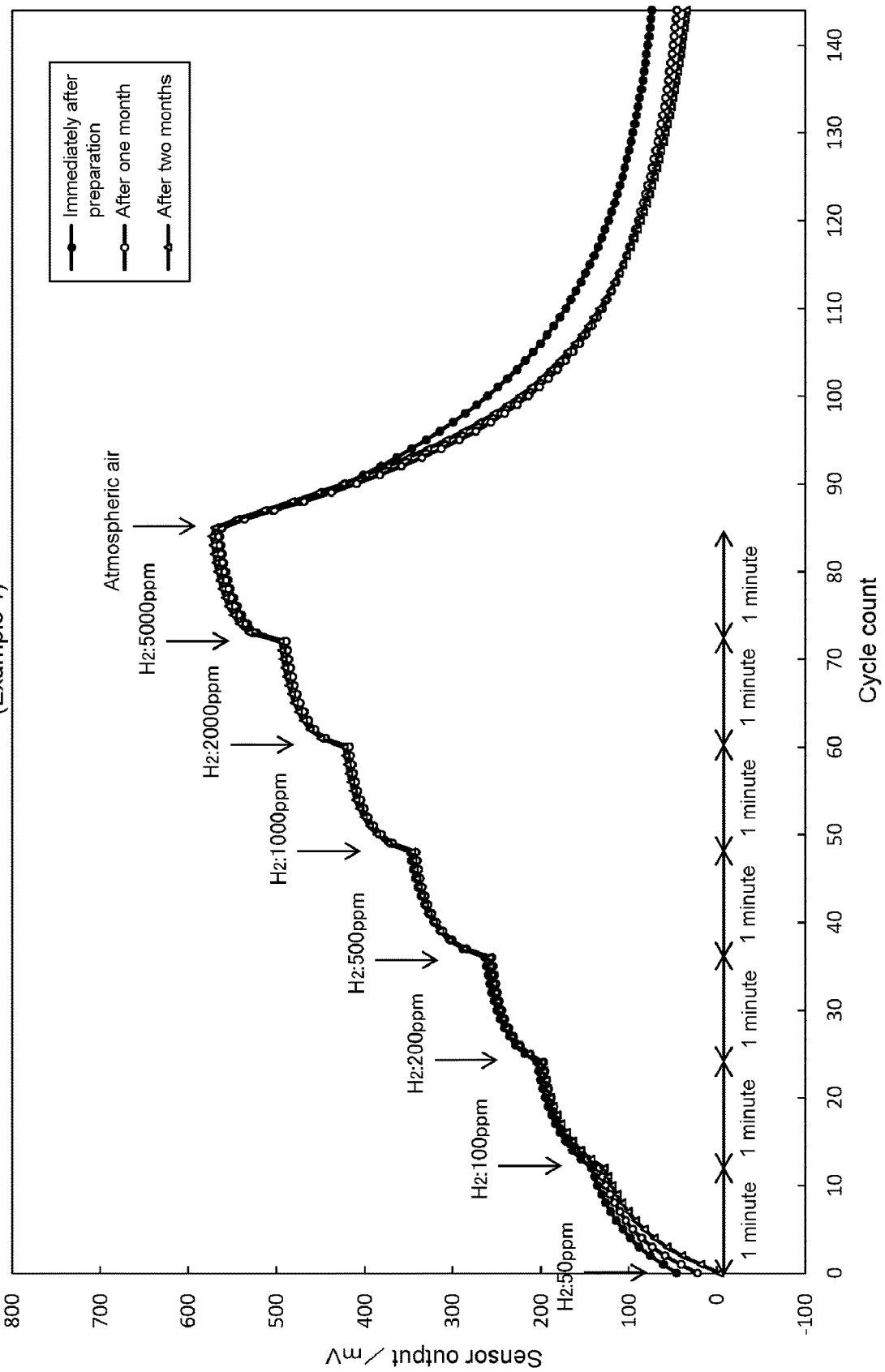
FIG. 3 is a graph showing results of measurement of sensor output changes of the MEMS type semiconductor gas detection element of Example 1 to hydrogen gas concentration changes.
Figure 4:
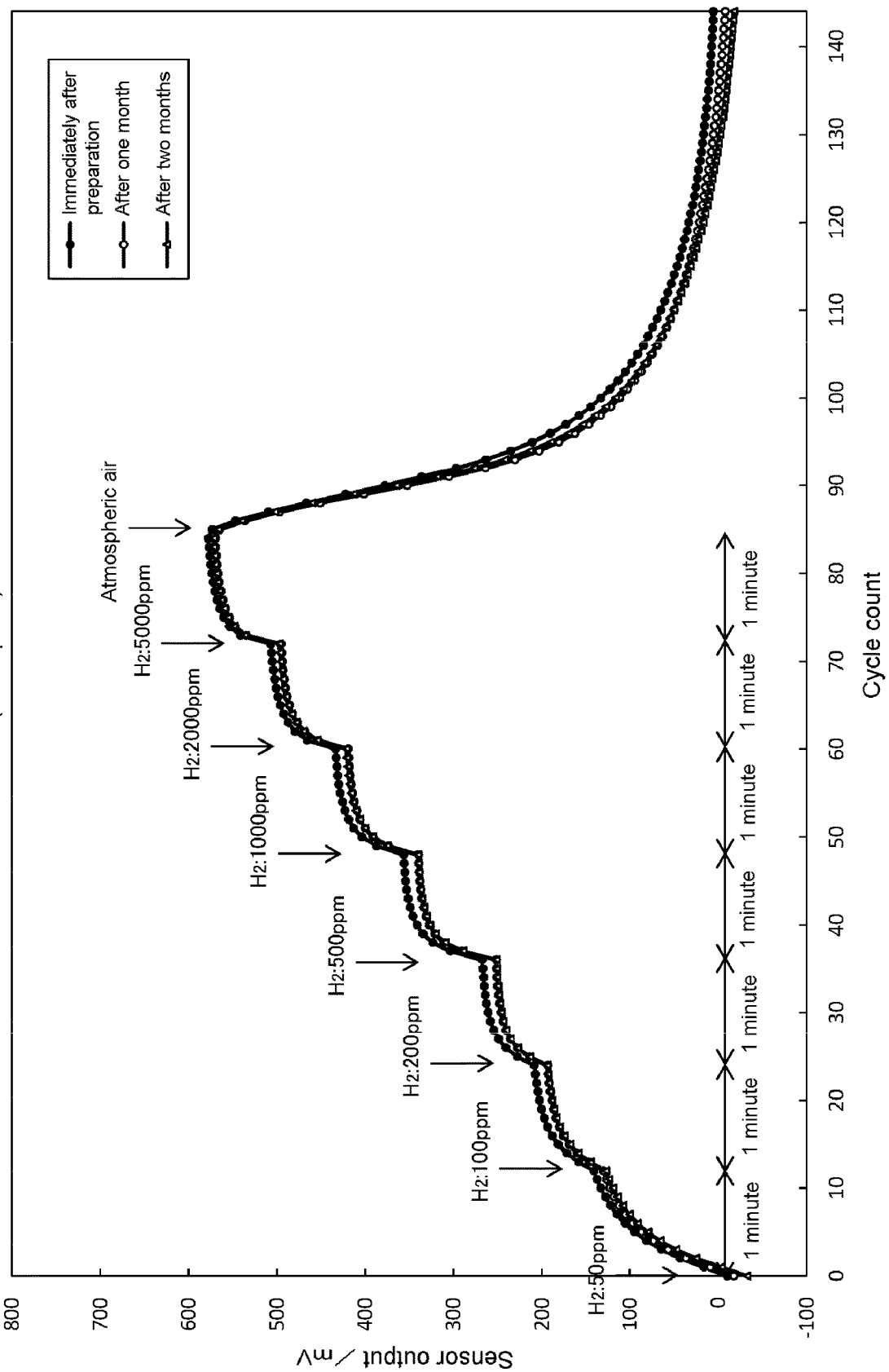
FIG. 4 is a graph showing results of measurement of sensor output changes of the MEMS type semiconductor gas detection element of Example 2 to hydrogen gas concentration changes.
Figure 5:
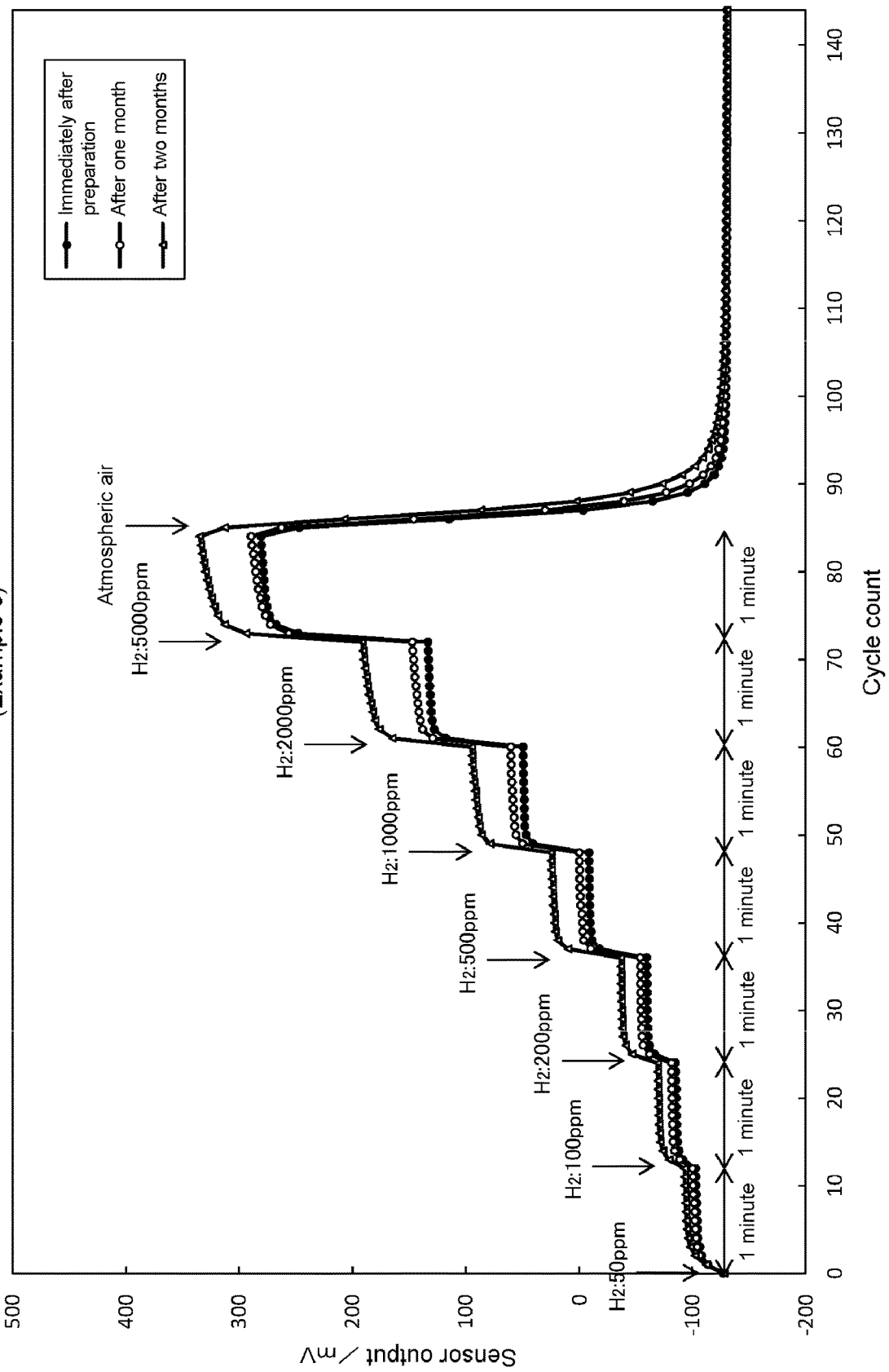
FIG. 5 is a graph showing results of measurement of sensor output changes of the MEMS type semiconductor gas detection element of Example 3 to hydrogen gas concentration changes.
Figure 6:
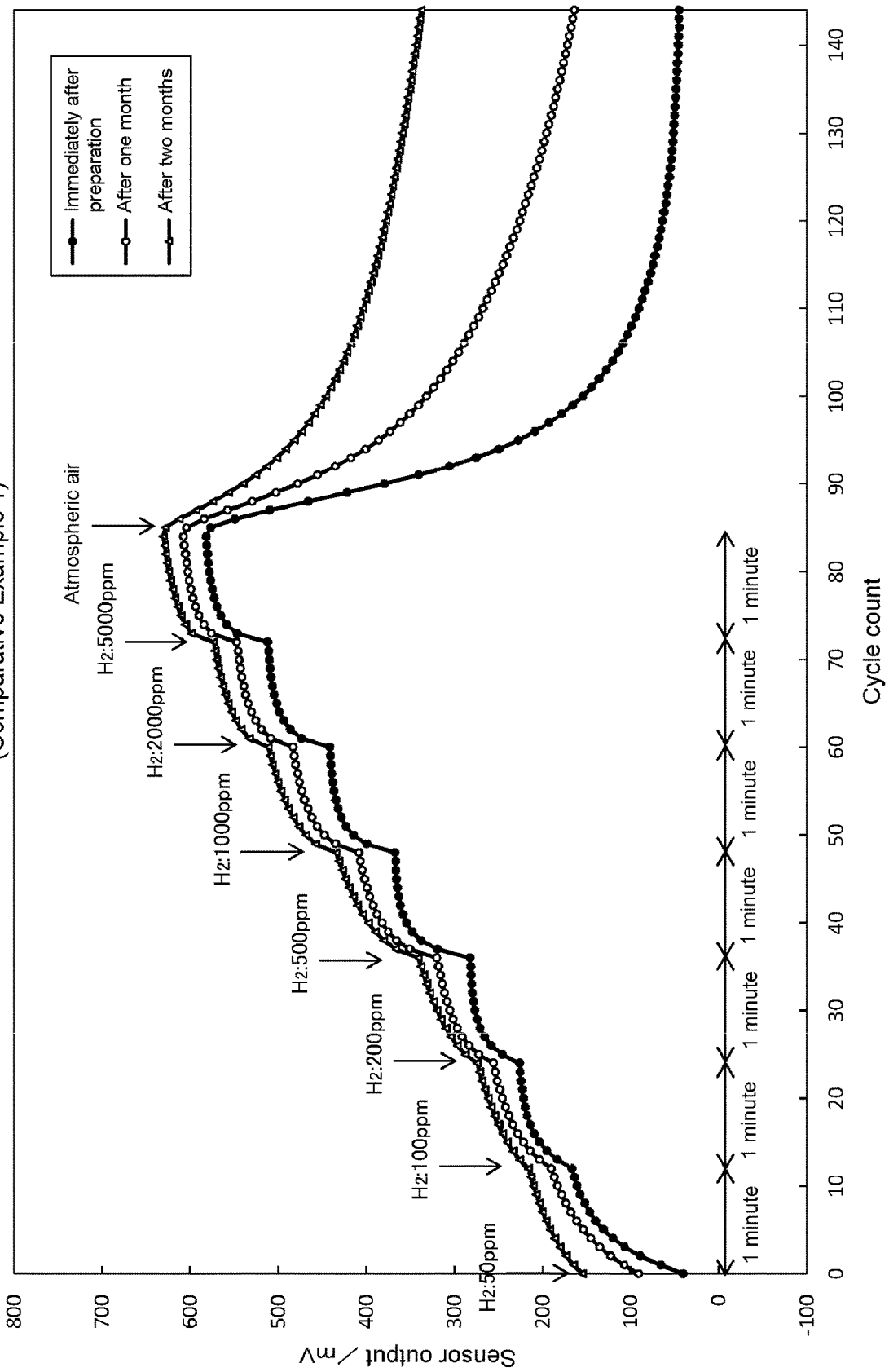
FIG. 6 is a graph showing results of measurement of sensor output changes of the MEMS type semiconductor gas detection element of Comparative Example 1 to hydrogen gas concentration changes.

FIGS. 3 to 5 show measurement results of Examples 1 to 3, where the gas sensitive portion was made of tin oxide semiconductor, and FIG. 6 shows a measurement result of Comparative Example 1, where similarly the gas sensitive portion was made of tin oxide semiconductor. It is to be noted that, in each figure, each of the timings when the hydrogen gas concentration in the atmospheric air was increased and the timing when the environmental atmosphere was replaced with the atmospheric air are indicated by arrows.

Referring to FIG. 6 of Comparative Example 1, immediately after the preparation of Comparative Example 1, the sensor output increases comparatively quickly at each timing of increases of the hydrogen gas concentration, and the sensor output declines comparatively quickly at the timing when the environmental atmosphere was replaced with the atmospheric air. This result shows that, in Comparative Example 1, the response characteristic and response recovery characteristic is obtained within a predetermined range immediately after the preparation. However, as time passed by one month and two months since the preparation of Comparative Example 1, the increases of the sensor output at each timing of increases of the hydrogen gas concentration became gradual, and the decline of the sensor output at the timing when the environmental atmosphere was replaced with the atmospheric air became gradual. Especially, for the decline of the sensor output at the timing when the environmental atmosphere was replaced with the atmospheric air, the sensor output did not return to the sensor output before the start of the measurement within this measurement cycle. This result shows that, in Comparative Example 1, the response characteristic and response recovery characteristic significantly deteriorated over time.

In contrast, referring to FIGS. 3 to 5 of Examples 1 to 3, where the protective film was provided to Comparative Example 1, little changes are observed in the increases of the sensor output at each timing of increases of the hydrogen gas concentration and the decline of the sensor output at the timing when the environmental atmosphere was replaced with the atmospheric air, even one month, two months passed after the preparation of Examples 1 to 3. This result shows that the deterioration over time of the response characteristic and response recovery characteristic was suppressed by providing the protective film. Especially, regarding Example 3 (FIG. 5) having the protective film made of a carrier made of aluminosilicate carrying chromium oxide, immediately after the preparation, there are shown steep changes in the increases of the sensor output at each timing of increases of the hydrogen gas concentration and the decline of the sensor output at the timing when the environmental atmosphere was replaced with the atmospheric air, compared to Comparative Example 1 (FIG. 6). This result shows that the excellent response characteristic and response recovery characteristic can be obtained immediately after the preparation of the element by using the protective film made of the carrier made of aluminosilicate carrying chromium oxide. It is considered that this may be because interference gases other than hydrogen gas were decomposed by chromium oxide having high oxidation activity in the protective film and inhibited from reaching to the inactive film.

Figure 7:
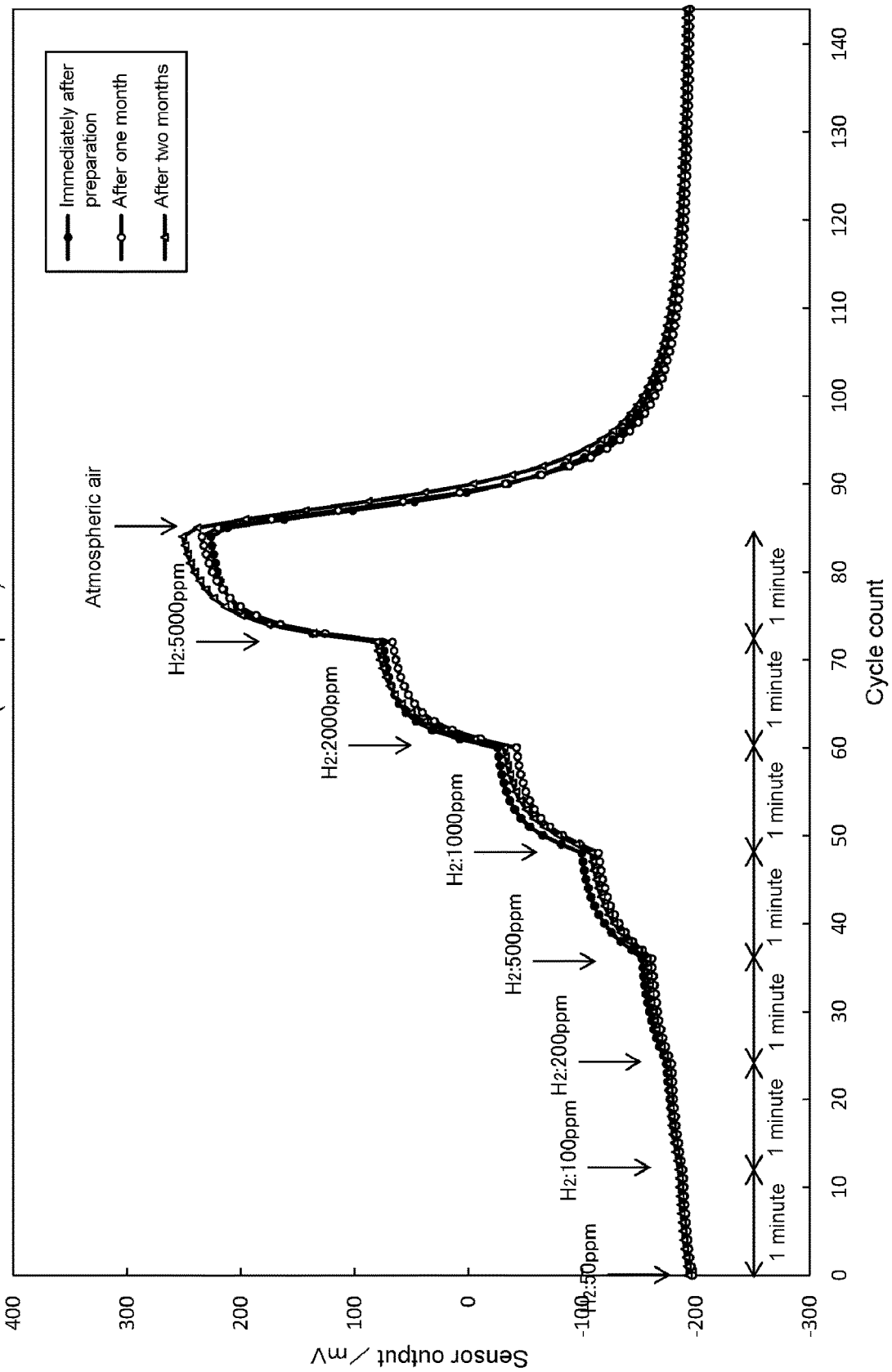
FIG. 7 is a graph showing results of measurement of sensor output changes of the MEMS type semiconductor gas detection element of Example 4 to hydrogen gas concentration changes.
Figure 8:
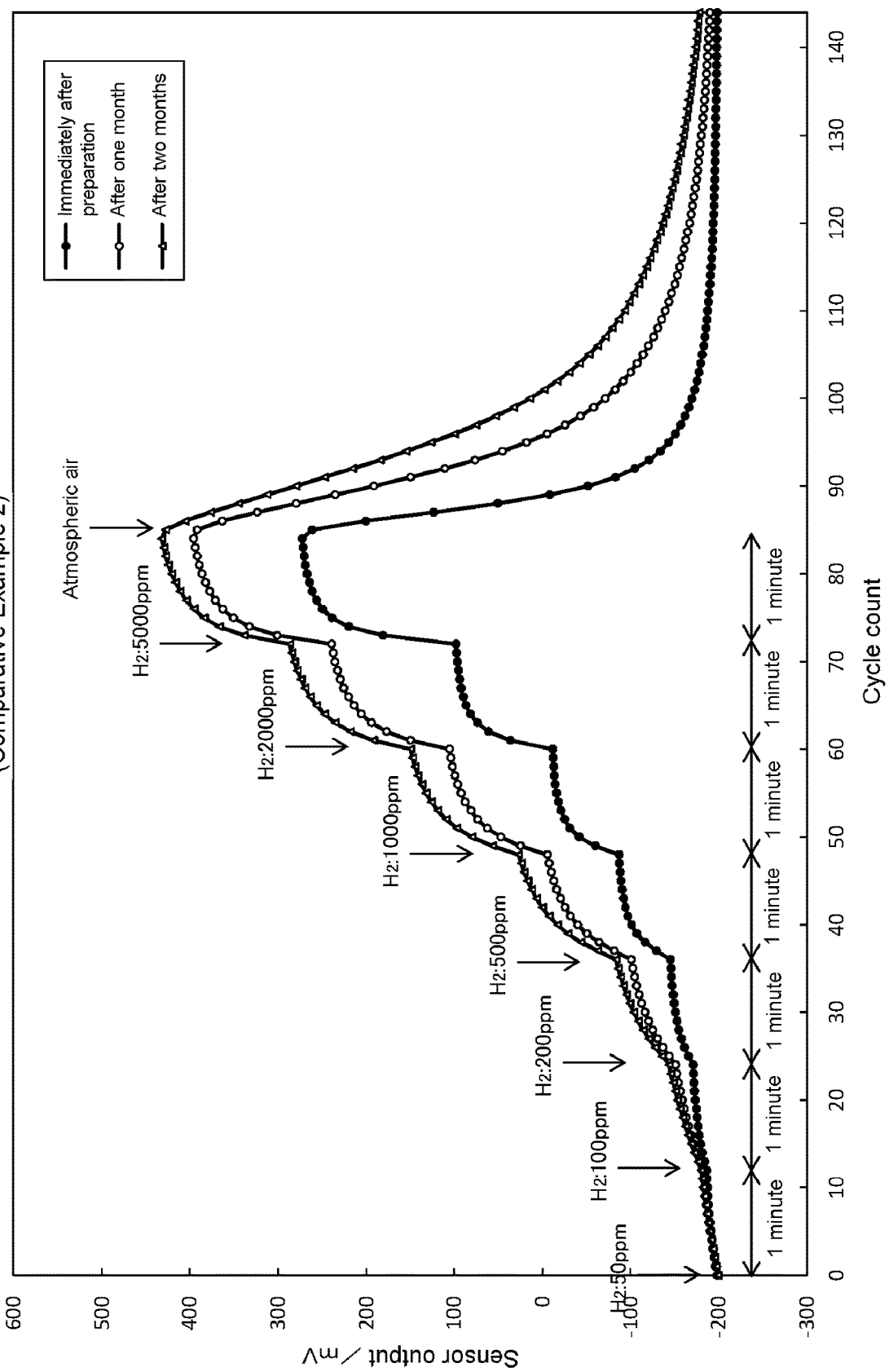
FIG. 8 is a graph showing results of measurement of sensor output changes of the MEMS type semiconductor gas detection element of Comparative Example 2 to hydrogen gas concentration changes.

FIG. 7 shows a measurement result of Example 4, where the gas sensitive portion 3 is made of tin oxide semiconductor carrying chromium oxide, and FIG. 8 shows a measurement result of Comparative Example 2, where similarly the gas sensitive portion 3 is made of tin oxide semiconductor carrying chromium oxide. It is to be note that, in these figures, as mentioned above, each of the timings when the hydrogen gas concentration in the atmospheric air was increased and the timing when the environmental atmosphere was replaced with the atmospheric air are indicated by arrows.

Referring to FIG. 8 of Comparative Example 2, in the result immediately after the preparation of Comparative Example 2, compared to the result immediately after the preparation of Comparative Example 1 (FIG. 6), the sensor output rapidly increased at each of the timings when the hydrogen gas concentration was increased, and the sensor output rapidly declined at the timing when the environmental atmosphere was replaced with the atmospheric air. This result shows that, in the result immediately after the preparation of Comparative Example 2, the excellent response characteristic and response recovery characteristic can be obtained, compared to Comparative Example 1. It is considered that this may be because the absorption activity of water molecules to tin oxide semiconductor of the gas sensitive portion was suppressed to stabilize the oxidation activity of tin oxide semiconductor since chromium oxide, which was metal oxide having high oxidation activity, was added to the gas sensitive portion. On the other hand, as one month and two months passed since the preparation of Comparative Example 2, the increases of the sensor output at each timing of increases of the hydrogen gas concentration became gradual, and the decline of the sensor output at the timing when the environmental atmosphere was replaced with the atmospheric air became gradual. This result shows that, in Comparative Example 2, the response characteristic and response recovery characteristic deteriorated over time.

In contrast, referring to FIG. 7 of Example 4, where the protective film was provided to Comparative Example 2, little changes are observed in the increases of the sensor output at each timing of increases of the hydrogen gas concentration and the decline of the sensor output at the timing when the environmental atmosphere was replaced with the atmospheric air, even one month, two months passed after the preparation of Example 4. This result shows that the deterioration over time of the response characteristic and response recovery characteristic was suppressed by providing the protective film.

(Evaluation of Changes Over Time in the Detection Sensitivity to Hydrogen Gas)

With the MEMS type semiconductor gas detection elements of Examples 1, 2, 4 and Comparative Examples 1, 2 incorporated in a known bridge circuit, changes over time in the sensor output to the different hydrogen gas concentrations were measured. Further, changes over time in the sensor output to the different methane gas concentrations were also measured to evaluate the hydrogen gas selectivity of the MEMS type semiconductor gas detection elements. The driving condition of the MEMS type semiconductor gas detection elements was a pulse drive having a pattern of 0.06 seconds of voltage applying in a cycle of 5 seconds so that the temperature during heating was 500° C. As the sensor output, the value at the time when the sensor output value was stabilized since the start of measurement was adopted.

The measurement environmental atmospheres were as follows: (1) an atmospheric air; (2) the hydrogen gas concentrations in the atmospheric air: 50 ppm, 100 ppm, 200 ppm, 500 ppm, 1000 ppm, 2000 ppm, 5000 ppm; (3) the methane gas concentrations in the atmospheric air: 1000 ppm, 2000 ppm, 5000 ppm. The changes over time in the sensor output were evaluated by conducting the above-mentioned measurement at an interval of several days for a period of about two months from immediately after the preparation of the MEMS type semiconductor gas detection elements.

Figure 9:
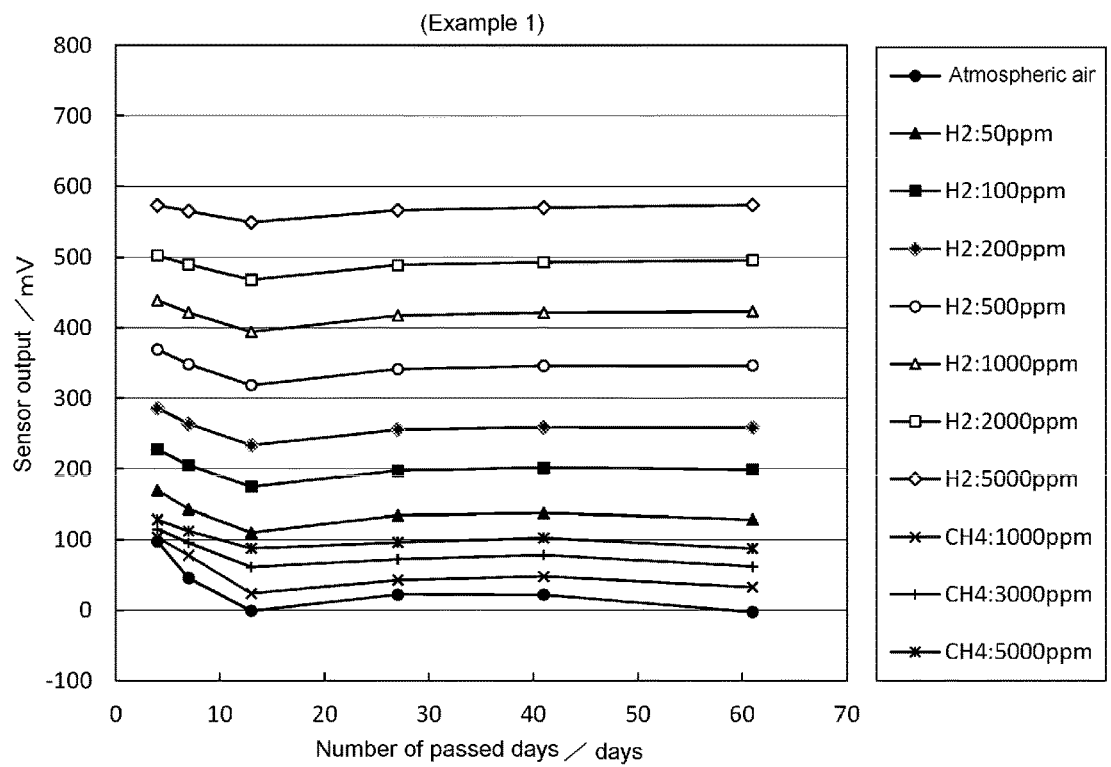
FIG. 9 is a graph showing results of measurement of changes over time in the sensor output of the MEMS type semiconductor gas detection element of Example 1 to hydrogen gas and methane gas.
Figure 10:
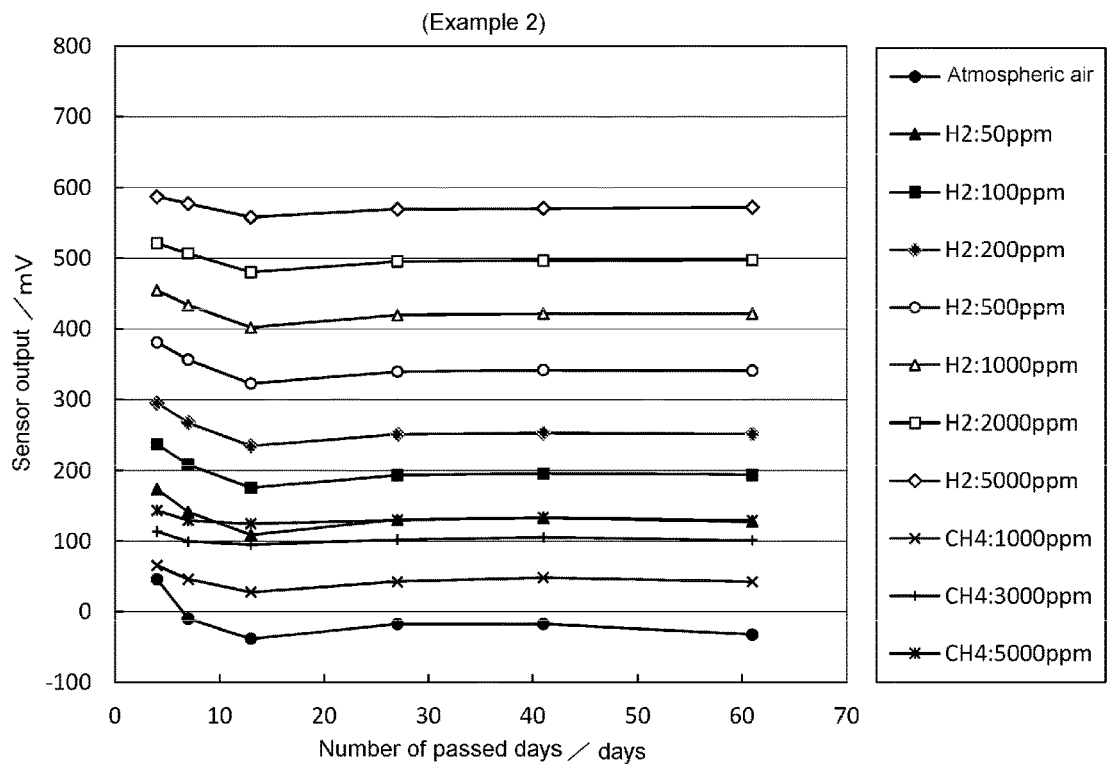
FIG. 10 is a graph showing results of measurement of changes over time in the sensor output of the MEMS type semiconductor gas detection element of Example 2 to hydrogen gas and methane gas.
Figure 11:
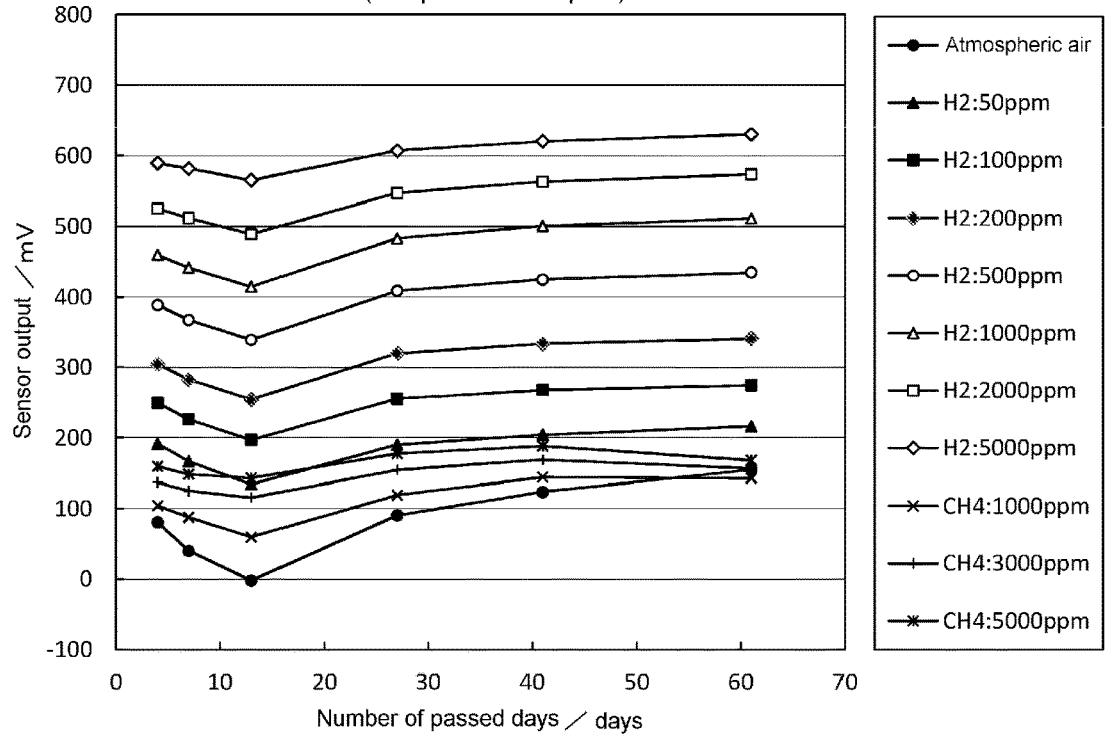
FIG. 11 is a graph showing results of measurement of changes over time in the sensor output of the MEMS type semiconductor gas detection element of Comparative Example 1 to hydrogen gas and methane gas.

FIGS. 9, 10 show measurement results of Examples 1, 2, where the gas sensitive portion was made of tin oxide semiconductor. FIG. 11 shows Comparative Example 1, where similarly the gas sensitive portion was made of tin oxide semiconductor. Examples 1, 2 of FIGS. 9, 10 and Comparative Example 1 of FIG. 11 have a difference in whether or not they have the protective film. Referring to FIG. 11 of Comparative Example 1, in any of the concentrations of hydrogen gas, the sensor output declined once immediately after the preparation of the element, and then increased as time passed. This result shows that, in Comparative Example 1, the detection sensitivity to hydrogen gas changed over time. In contrast, referring to FIGS. 9, 10 of Examples 1, 2, where the protective film was provided to Comparative Example 1, in any of the concentrations of hydrogen gas, the sensor output slightly declined immediately after the preparation of the element, and then showed an approximately constant value as time passed. This result shows that, in Examples 1, 2, the changes over time in the detection sensitivity to hydrogen gas, which were occurred in Comparative Example 1, can be suppressed by providing the protective film. It is to be noted that the sensor output when the atmospheric air contains methane gas was significantly smaller than the sensor output for hydrogen gas of the same concentration, and this result shows that the hydrogen gas selectivity was maintained in any of the concentrations.

Figure 12:
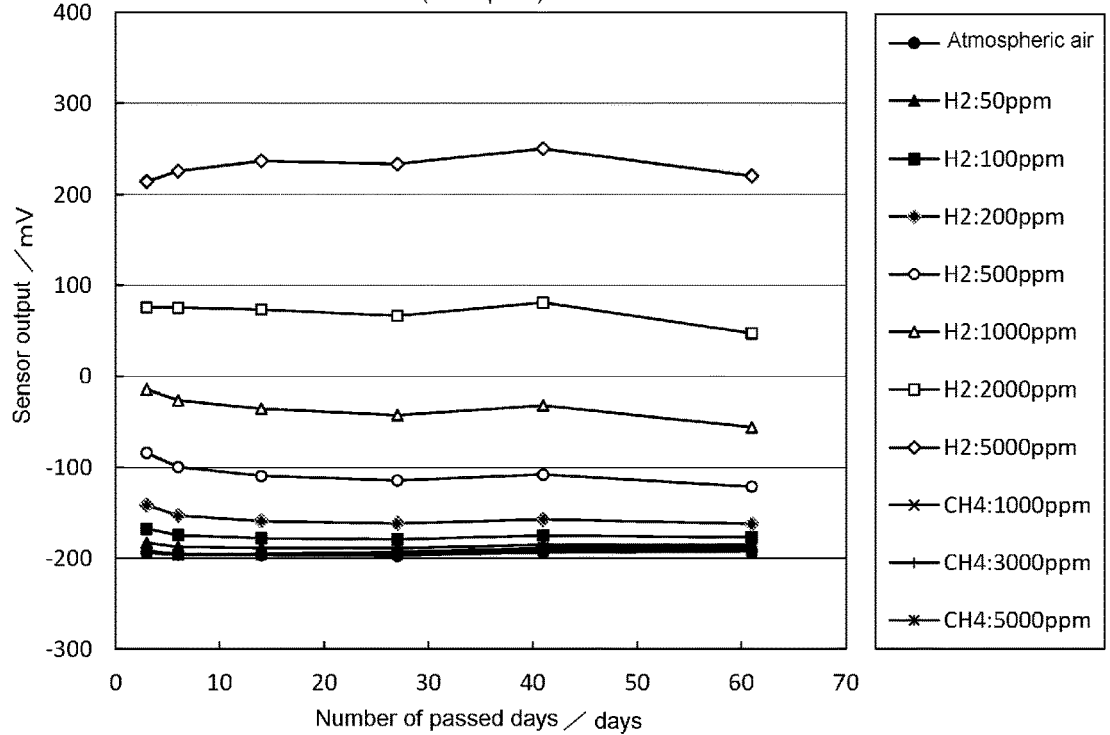
FIG. 12 is a graph showing results of measurement of changes over time in the sensor output of the MEMS type semiconductor gas detection element of Example 4 to hydrogen gas and methane gas.
Figure 13:
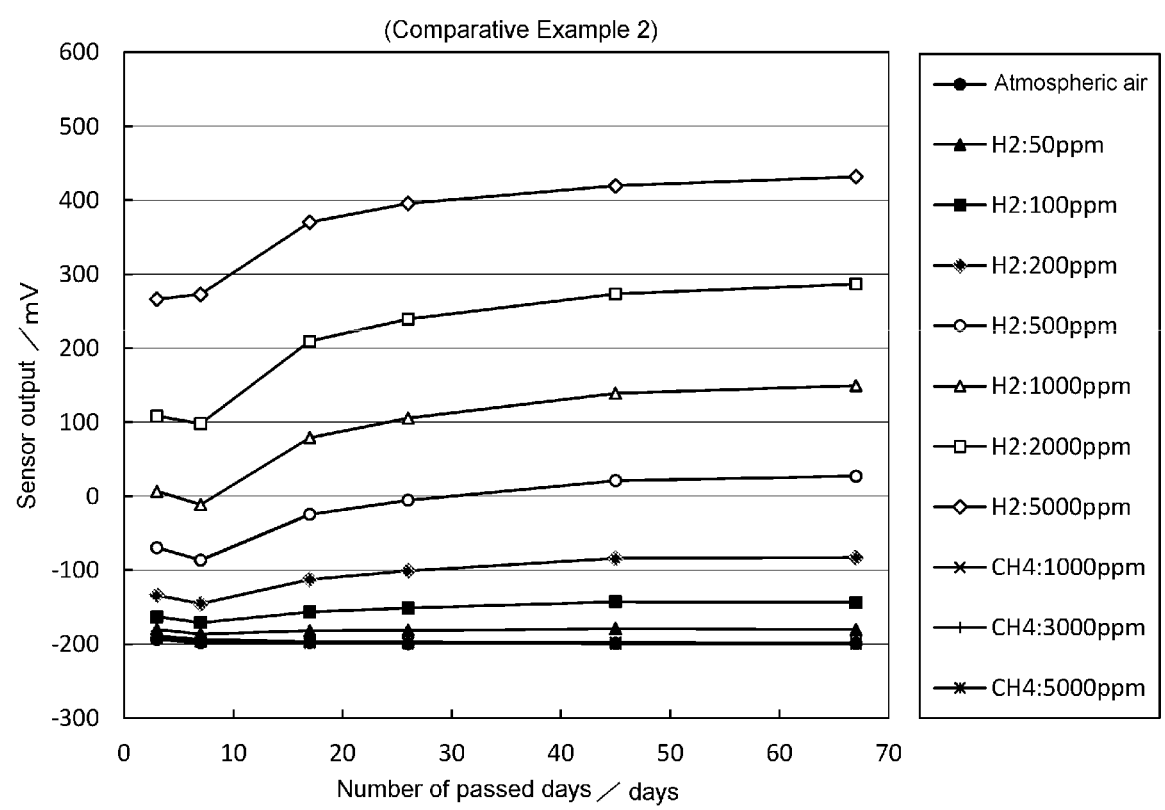
FIG. 13 is a graph showing results of measurement of changes over time in the sensor output of the MEMS type semiconductor gas detection element of Comparative Example 2 to hydrogen gas and methane gas.

FIG. 12 shows a measurement result of Example 4, where the gas sensitive portion was made of tin oxide semiconductor carrying chromium oxide. FIG. 13 shows a measurement result of Comparative Example 2, where similarly the gas sensitive portion was made of tin oxide semiconductor carrying chromium oxide. Example 4 of FIG. 12 and Comparative Example 2 of FIG. 13 have a difference in whether or not they have the protective film. Referring to FIG. 13 of Comparative Example 2, in any of the concentrations of hydrogen gas, the sensor output increased from immediately after the preparation of the element as time passed. This result shows that, in Comparative Example 2, the detection sensitivity to hydrogen gas changed over time. In contrast, referring to FIG. 12, where the protective film was provided to Comparative Example 2, in any of the concentrations of hydrogen gas, the sensor output showed an approximately constant value as time passed. This result shows that, in Example 4, the changes over time in the detection sensitivity to hydrogen gas, which were occurred in Comparative Example 2, can be suppressed by providing the protective film. It is to be noted that the sensor output when the atmospheric air contains methane gas was significantly smaller than the sensor output for hydrogen gas of the same concentration, and this result shows that the hydrogen gas selectivity was maintained in any of the concentrations.

As shown above, the MEMS type semiconductor gas detection element 1 of the embodiment can suppress deterioration of the gas sensitive portion while maintaining the hydrogen selectivity by comprising a substrate 2; a gas sensitive portion 3 mainly made of a metal oxide semiconductor and provided to the substrate 2; a heating portion 4 for heating the gas sensitive portion 3; an inactive film having hydrogen-permselective and formed outside the gas sensitive portion 3; and a protective film 6 formed outside the inactive film 5, for suppressing deterioration of the gas sensitive portion 3.

LIST OF REFERENCE SIGNS

1 MEMS type semiconductor gas detection element
2 substrate
21 substrate main body
22 insulating support layer
23 cavity portion
3 gas sensitive portion
4 heating portion
5 inactive film
6 protective film
A laminated body

The invention claimed is:

1. A MEMS type semiconductor gas detection element having a MEMS structure, for detecting hydrogen gas, comprising:
   a substrate;
   a gas sensitive portion mainly made of a metal oxide semiconductor and provided to the substrate;
   a heating portion for heating the gas sensitive portion;
   an inactive film having hydrogen-permselective and formed outside the gas sensitive portion; and
   a protective film formed outside the inactive film, for suppressing deterioration of the gas sensitive portion, characterized in that
   the inactive film comprises a silica film having a siloxane bond, and
   the protective film comprises alumina or a complex oxide containing aluminum and silicon.

2. The MEMS type semiconductor gas detection element of claim 1, characterized in that the protective film is configured to suppress deterioration over time of a response characteristic and/or response recovery characteristic of the gas sensitive portion to hydrogen gas.

3. The MEMS type semiconductor gas detection element of claim 1, characterized in that the inactive film is formed at a part of the gas sensitive portion.

4. The MEMS type semiconductor gas detection element of claim 1, characterized in that the inactive film is formed at an outer surface part of the gas sensitive portion.

5. The MEMS type semiconductor gas detection element of claim 1, characterized in that the protective film is made of a carrier made of a complex oxide containing aluminum and silicon carrying chromium oxide or palladium oxide.

\* \* \* \* \*